United States Patent [19]
Popitz

[11] Patent Number: 5,857,460
[45] Date of Patent: Jan. 12, 1999

[54] GAS-SENSING MASK

[75] Inventor: Michael D. Popitz, Dover, Mass.

[73] Assignee: Beth Israel Deaconess Medical Center, Inc., Boston, Mass.

[21] Appl. No.: 615,892

[22] Filed: Mar. 14, 1996

[51] Int. Cl.[6] .......................... A62B 18/02; A62B 18/08; A61M 16/00
[52] U.S. Cl. ............... 128/206.21; 128/206.28; 128/206.12; 128/204.22; 128/204.23; 128/205.25; 128/205.28
[58] Field of Search ................ 128/204.22, 204.23, 128/205.23, 205.25, 205.28, 206.12, 206.17, 206.21, 206.28; 385/12

[56] References Cited

U.S. PATENT DOCUMENTS

| | | |
|---|---|---|
| 2,843,121 | 7/1958 | Hudson . |
| 2,848,994 | 8/1958 | Aguado . |
| 3,395,701 | 8/1968 | Bartlett, Jr., et al. ............. 128/204.23 |
| 3,675,649 | 7/1972 | Basham et al. . |
| 4,579,113 | 4/1986 | McCreadie et al. ............. 128/202.13 |
| 4,691,701 | 9/1987 | Williams . |
| 4,728,499 | 3/1988 | Fehder . |
| 4,790,327 | 12/1988 | Despotis . |
| 4,879,999 | 11/1989 | Leiman et al. . |
| 4,932,402 | 6/1990 | Snook et al. ............. 128/204.23 |
| 4,945,918 | 8/1990 | Abernathy . |
| 4,994,117 | 2/1991 | Fehder . |
| 5,005,572 | 4/1991 | Raemer et al. . |
| 5,012,805 | 5/1991 | Muckerheide . |
| 5,046,491 | 9/1991 | Derrick ............. 128/200.24 |
| 5,179,002 | 1/1993 | Fehder . |
| 5,279,289 | 1/1994 | Kirk . |
| 5,315,673 | 5/1994 | Stetter et al. ............. 385/12 |
| 5,375,592 | 12/1994 | Kirk et al. . |
| 5,400,781 | 3/1995 | Davenport ............. 128/206.28 |
| 5,474,060 | 12/1995 | Evans ............. 128/204.22 |

FOREIGN PATENT DOCUMENTS

| | | |
|---|---|---|
| 3707952A1 | 9/1988 | Germany . |
| 4329031A1 | 9/1994 | Germany . |

*Primary Examiner*—Aaron J. Lewis
*Assistant Examiner*—Dinh X. Nguyen
*Attorney, Agent, or Firm*—Lahive & Cockfield, LLP

[57] ABSTRACT

A gas sensing mask and system which senses and indicates the presence or absence of a selected respired gas. The mask includes a non-porous housing that is sized to seat over the nose and mouth of a subject. The mask includes a fluid aperture that is coupled to a fluid source and a sensor mounting aperture formed in an intermediate portion of the housing. A gas sensor, which senses one or more selected gases respired by the subject, is directly mounted within the sensor mounting aperture. The gas sensor includes a calorimetric indicator which visually indicates the presence or absence of the respired gas.

18 Claims, 4 Drawing Sheets

GAS-SENSING MASK

BACKGROUND OF THE INVENTION

The present invention generally relates to fluid delivery systems, and more particularly to fluid delivery systems that administer oxygen or other suitable gases to a patient.

Each year relatively large numbers of individuals suffer from some type of acute distress which requires treatment at hospitals or by emergency response personnel. Often times, in order to stabilize the individual during the distress period, it is necessary to supplement the individual's oxygen intake to facilitate the breathing of the individual. Once the patient is treated and stabilized, the patient may still require a supplemental oxygen supply. In such cases, it is important to monitor the breathing rate of the individual to ensure continuous respiration and proper oxygen uptake. Hence, if the acute distress reoccurs, which can result in difficulty or a complete cessation of breathing, the hospital clinicians or emergency response personnel can quickly recognize the situation and respond accordingly.

There presently exists several conventional practices for administering oxygen to facilitate breathing of a patient in distress. One practice includes the use of a looped cannula having a pair of stub-like portions which are placed within the nostrils of the patient. Oxygen is introduced to the patient through these stub-like portions. Typical drawbacks of using the cannula include irritation of the nose, which causes swelling and at times severe discomfort, particularly if the person is allergic to the long term presence of the cannula. Another drawback is that the cannula can become easily crimped, thus cutting off the oxygen supply to the patient. Further drawbacks include the relatively easy dislodgment of the cannula from the patient's nostrils.

A variety of oxygen masks have also been used to administer oxygen to the patient. The oxygen masks vary in type and construction depending upon the specific purpose or use of the mask. Conventional oxygen masks include a body, either resilient or rigid, that is sized to seat over the face of the patient. Oxygen is introduced to the patient through an oxygen inlet, and respired gases are vented from the mask interior through appropriately placed ventilation apertures.

Other conventional oxygen administering apparatuses include oxygen tents which substantially completely surround the patient's head. The oxygen tent includes a support structure that supports a resilient membrane (which forms an oxygen chamber) about the patient's head. Oxygen is supplied to the interior of the chamber by appropriately placed fluid conduits. A drawback of the oxygen tent is that a relatively significant portion of the oxygen can escape from the tent. Thus, the total amount of oxygen supplied to the patient is not readily determinable. Furthermore, the creation of a highly flammable environment about the patient's head exposes the patient to risk of injury.

The industry has also developed a number of carbon dioxide indicators which detect the presence of carbon dioxide in a gas mixture. These carbon dioxide detection apparatuses include a chemical compound that changes color in the presence of carbon dioxide. Other devices include pH sensitive dyes suspended in a gel substance, and gas analyzers which typically employ a light source to transmit light through a multi-layered sensor unit and a detector to receive and analyze the color changes of a pH sensitive indicator disposed in one or more of the layers. These devices are commonly used, however, in conjunction with endotrachial tubes to determine whether correct intubation procedures have been effected. Examples of such carbon dioxide indicators are shown and described in U.S. Pat. No. 4,728,499 of Fehder, U.S. Pat. No. 4,994,117 of Fehder, and U.S. Pat. No. 5,375,592 of Kirk et al.

A common drawback of the foregoing conventional oxygen-administering and endotracheal devices is that they generally do not monitor, over a period of time, the breathing or respiration of the patient.

Due to the foregoing and other shortcomings of prior art oxygen administering and gas detecting devices, it is thus an object of the present invention to provide a system for continuously monitoring the respiration of a patient.

It is another object of the invention to provide a relatively lightweight and relatively low cost gas-sensing device suitable for use in hospital and home care environments.

Still another object of the invention is to provide a system and apparatus that continuously detects changes in the respiratory rate of a subject wearing a gas delivery system.

Yet another object of the invention is to provide a system and apparatus that provides a visual indicator of the respiration of the patient.

Still yet another object of the invention is to provide apparatus that detects and displays or indicates the respiratory rate of the subject.

Another object of the invention is to provide a relatively reliable and inexpensive apparatus that monitors the breathing rate of the subject.

Other general and more specific objects of the invention will in part be obvious and will in part appear from the drawings and description which follow.

SUMMARY OF THE INVENTION

The present invention provides for a gas sensing mask and system that senses the presence or absence of a selected respired gas, e.g., carbon dioxide, and that indicates the presence or absence thereof. The term "respired gas" is intended to include any gas inhaled or exhaled by the patient, and particularly includes oxygen and carbon dioxide. The invention attains the foregoing and other objects with a gas sensing mask that includes a non-porous housing that is sized to seat over the nose and mouth of a subject. The mask includes a fluid aperture which communicates with a fluid source and a sensor mounting aperture formed in an intermediate portion of the housing. A gas sensor, which senses one or more selected respired gases, is directly mounted within the sensor mounting aperture. The sensor when mounted within the mounting aperture of the mask is integral with the housing and is preferably disposed in intimate contact therewith.

According to one aspect, the gas sensor includes an indicator element that is integral with the gas sensor, and which visually indicates the presence or absence of the respired gas. According to one practice, the gas sensor includes a calorimetric element that calorimetrically indicates the presence or absence of the gas. The gas sensor thus changes color in the presence of a respired gas, and particularly changes color in the presence of carbon dioxide. According to another practice, the gas sensor includes a gas-sensitive element, e.g., a pH-sensitive electrode or transistor, that forms part of the gas sensor or is coupled to the mask. The gas-sensitive element produces an electrical signal in response to the presence of carbon dioxide. The element is coupled to a control unit that is responsive to the electrical signals produced by the element, and which in turn is coupled to one or more means for indicating the presence or absence of the gas, including an audible alarm or visual alarm or monitor. The mask thus allows attending clinicians to monitor the respiration of the subject while concomitantly allowing the clinicians to be remotely located from the patient.

According to a preferred practice, the gas sensor includes a carbon-dioxide sensor that senses end-tidal carbon dioxide respired by the subject. The gas sensor includes chemical structure or compounds that calorimetrically indicates the presence or absence of the carbon dioxide, that is, the sensor generates a first color in the absence of carbon dioxide and a second, different color in the presence of carbon dioxide.

According to another aspect, the mask housing includes a substantially dome-shaped intermediate portion that forms a fluid chamber when the mask is mounted over the face of the subject. The mask further includes ventilation apertures formed in opposite sides of the mask for ventilating respired gases from the chamber to the external environment.

According to still another aspect, the gas sensor is removably and replaceably mounted within the sensor mounting aperture of the mask. The gas sensor is thus easily replaceable to facilitate repeated use of the mask housing. In an alternate embodiment, the gas sensor is permanently mounted within the mask, which is then disposed of after use.

According to another aspect, the mask includes a baffle element that is coupled to the mask for channeling respired gases to the sensor mounted within the sensor mounting aperture.

The present invention further pertains to a method for monitoring the respiration of the subject. More specifically, the invention pertains to a method for monitoring the respiration of a subject, which comprises the steps of (1) placing a non-porous mask over the mouth and nose of the subject, the mask having a first aperture formed therein; (2) sensing a selected respired gas from the subject by mounting a gas sensor mounted within the first aperture such that the sensor is integral with and disposed in intimate contact with the mask to visually indicate the presence of the respired gas; and (3) monitoring the respiration of the subject by the visual indication of the sensed respired gas.

Other general and more specific objects of the invention will in part be obvious and will in part be evident from the drawings and description which follow.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

DESCRIPTION OF ILLUSTRATED EMBODIMENT

Figure 1:
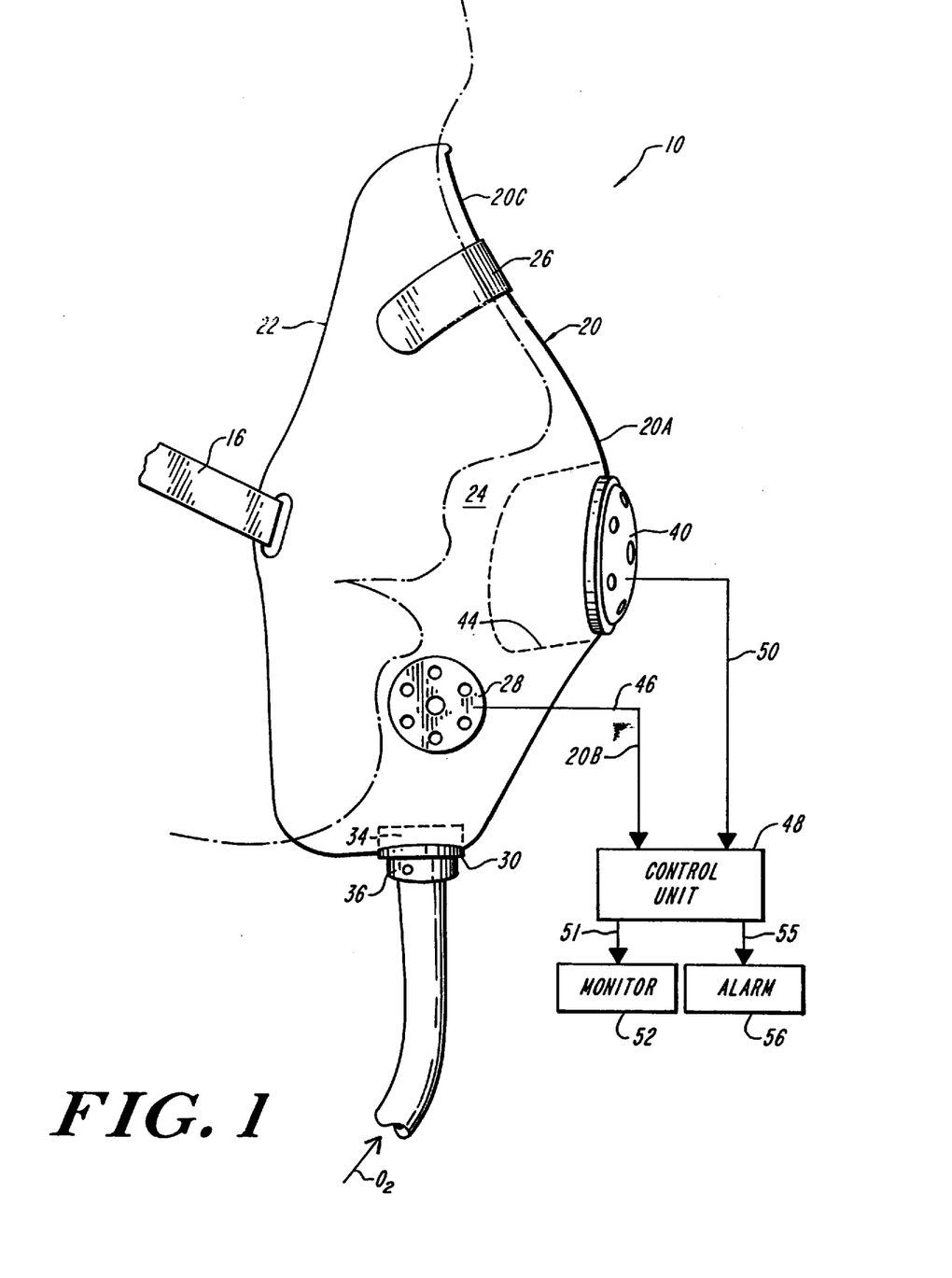
FIG. 1 is a perspective view of the fluid delivering, gas sensing mask of the present invention mounted on a patient.
Figure 2:
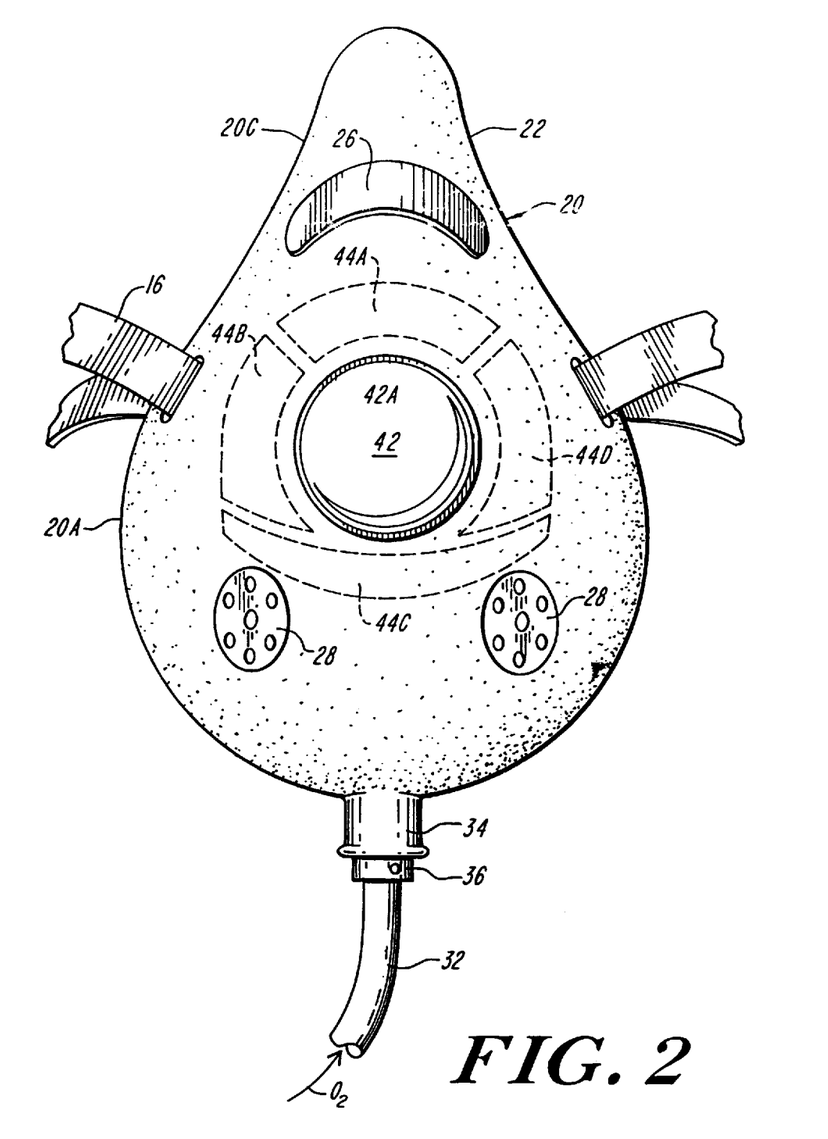
FIG. 2 is a top view of the gas mask of FIG. 1.
Figure 3:
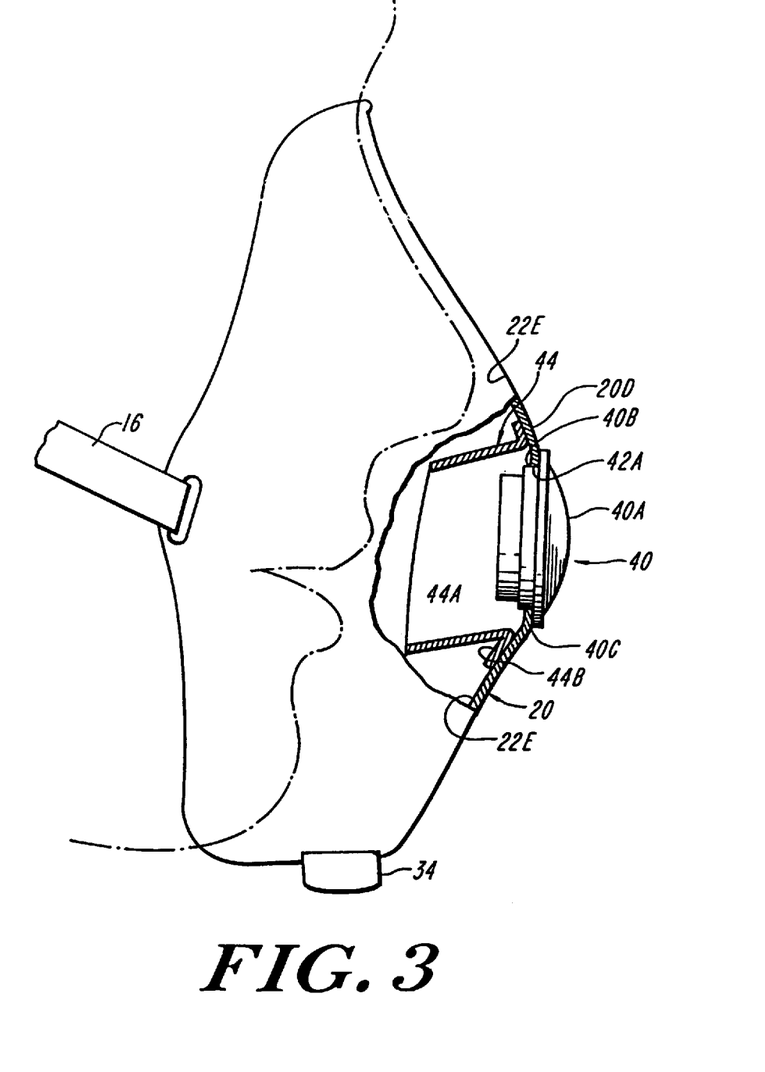
FIG. 3 is a partial fragmentary view of the gas mask of FIG. 1 showing the mounting of the sensor element and baffle plate within the interior of the mask.

FIGS. 1 through 3 illustrate a first embodiment of the gas-sensing mask 20 of the present invention mounted on a patient. The illustrated gas-sensing mask 20 includes a bottom portion 20B having formed therein a gas introducing aperture 30 that is coupled to a gas source, a pair of ventilation apertures 28, and a gas sensor 40 that is mounted within a sensor mounting aperture. A resilient flexible strap 16 can be coupled to the gas mask 20 by suitable strap apertures, and which serves to secure the gas mask 20 about the head of the patient.

The gas-sensing mask 20 can further be coupled to appropriate electrical control circuitry, illustratively as control unit 48 and associated gas-sensing elements (not shown), that senses a respired gas and controls one or more peripheral devices. The control unit 48 is coupled to the gas-sensing elements on the gas mask 20 via any suitable lead, such as by electrical leads 46 and 50. The control unit 48 is further electrically coupled to a conventional monitor 52 by electrical lead 51 and to an alarm unit by electrical lead 55. The alarm unit can be any conventional alarm which indicates, either audibly or visually, the respiratory state of the patient. The alarm unit can include an audible alarm, such as a buzzer, or any visual alarm, such as a light bulb or LED.

As illustrated in FIG. 1, the control unit 48 can be coupled to the gas-sensing mask 20 by electrical leads 46 or 50. The control unit 48 can be coupled to either the gas sensor 40 or to the mask housing, such as to ventilation aperture 28. The control unit, in conjunction with the gas sensing structure, senses one or more gases respired by the patient and which exits the gas mask through the ventilation aperture 28, or which contacts or exits the mask 20 through the gas sensor element 40.

The gas-sensing, fluid-delivering mask 20 preferably includes a top portion 20C, a dome-shaped intermediate portion 20A and a bottom portion 20B. The mask 20 further includes an outer peripheral portion 22 that covers a selected portion of the patient's face. The peripheral portion 22 contacts the patient's face when mounted thereon, and seats over the patient's nose and mouth such that the upper portion 20C seats over and contacts the brow of the nose and portions of the patient's cheekbone. As shown in FIGS. 1 and 2, the dome-shaped intermediate portion 20A of the mask 20 specifically overlies the nose and mouth while the outer peripheral edge 22 of the mask fans out (from top to bottom) to encompass further portions of the patient's cheek. The gas mask 20 also includes a tapered bottom portion 20B whose outer peripheral edge gradually tapers toward the chin portion of the patient. As illustrated in FIG. 1, when the mask 20 is mounted on the face of the patient, the outer peripheral edge 22 contacts selected portions of the face to minimize the amount of gas that escapes from the mask. As is known, secondary sealing structure can be mounted to the mask 20, such as over the brow of the nose, to form a substantially fluid-tight seal between the patient and the mask 20. This gas tight seal prevents oxygen from escaping through the upper portion of the mask 20. Thus, the seal functions as a redundant or supplemental fluid seal for the mask at locations where leakage is likely to occur. A benefit of providing a seal along the upper peripheral portion of the mask is that it prevents escaping oxygen from washing over the face of the patient and particularly into the patient's eyes.

The mask 20 can be formed of any suitable biologically compatible, non-porous material, such as plastic polymers, polypropanate, polycel urethane foam, polystyrene, polycarbonate plastics, polyvinylchloride and other vinyl compounds. The mask is preferably transparent.

With reference to FIGS. 1 and 3, the gas introducing aperture 30 preferably includes an integrally molded female luer portion 34. The female luer portion 34 is sized to seat a corresponding adapter 36. The adapter 36 is preferably integrally formed with the oxygen delivery tube 32, which in turn is coupled at an opposite end to an oxygen supply source. The mating connection between the adapter 36 and the female connector 34 forms a fluid-tight seal to prevent oxygen from escaping therefrom during delivery. The oxygen source preferably supplies oxygen to the fluid chamber 24 formed by the mask 20. The oxygen delivery system of the present invention is intended to include any suitable fluid delivery system that is compatible with the teachings of the present invention and which serves to deliver a fluid to the mask chamber. The delivery system is preferably disposed at a location that does not allow the inflowing oxygen to significantly mix with the respired gas of the patient, thus avoiding false readings by the gas sensor. Those of ordinary skill will appreciate the various permutations of the illustrated gas delivery system that are compatible with the mask of the present invention.

A pressure tab 26 is formed along the upper portion 20C of the mask 20 at a location that is disposed about an upper portion of the patient's nose. The pressure tab 26 conforms the shape of the masks to closely approximate the shape of the patient's face at the bridge of the nose. The pressure tab 26 in conjunction with the head strap 16 help secure the mask 20 to the patient's head.

The illustrated ventilation apertures 28 are formed in the lower portion 20B of the mask 20 on opposite sides thereof. The ventilation apertures provide a fluid pathway between the fluid chamber 24 and the external environment, thus allowing gases respired by the patient to exit the chamber 24 into the external environment.

Figure 4:
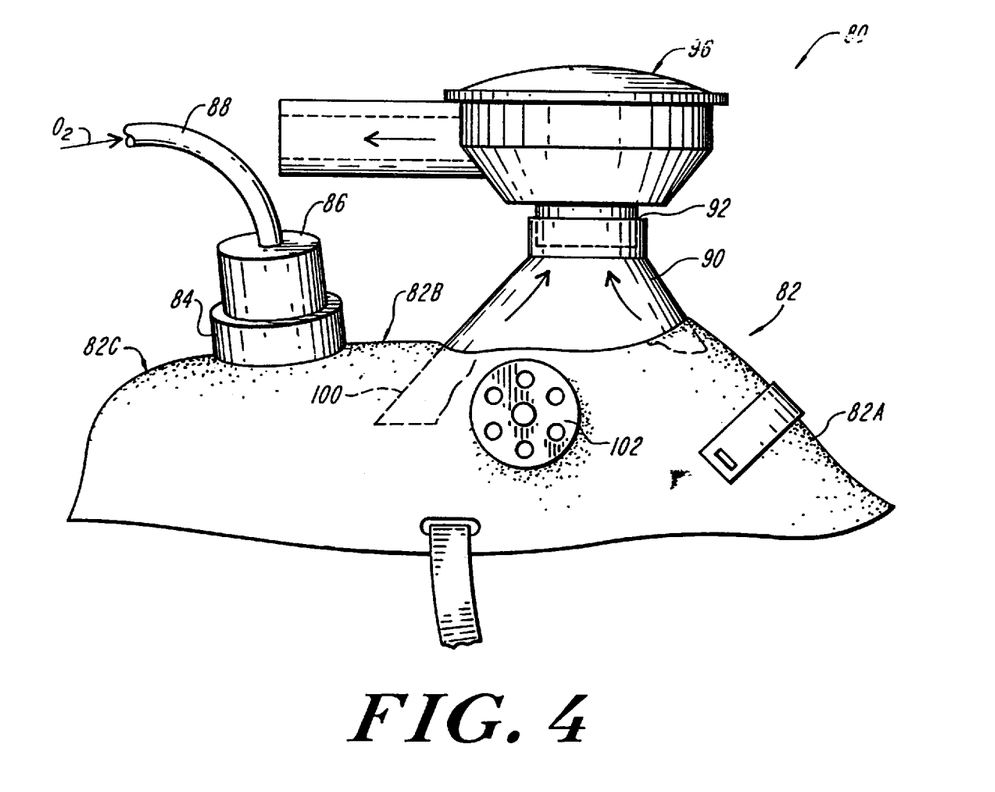
FIG. 4 is another embodiment of the fluid delivering, gas sensing mask of the present invention mounted on a patient.

The illustrated mask 20 further includes a sensor aperture 42 that is formed in the intermediate, dome-shaped region 20A of the mask 20. The aperture is preferably sized to seat a corresponding gas sensor 40 such that the inner peripheral surface 42A of the aperture intimately contacts the body portion 40B of the sensor 40, FIG. 3. According to one practice, when the gas sensor 40 is placed within the sensor aperture 42, an underside 40C of the gas sensor top portion 40A contacts the outer surface 20D of the gas mask. Those of ordinary skill will appreciate that a suitable sealing gasket can be disposed between the gas sensor 40 and the housing 20, and is thus also contemplated by the teachings of the present invention. The term "intimate contact" as used herein in relation to the mounting of the sensor within the aperture is intended to include the direct and contiguous mounting of the sensor within the aperture of the mask 20, such that the sensor either contacts the mask housing directly or contacts any suitable sealing structure that is coupled to the aperture. The sensor aperture can be formed directly in the mask housing (FIG. 1) or can be formed in an intermediate portion that mates with the mask housing (FIG. 4). It is thus contemplated that the term encompasses any particular mounting of the sensor with the sensor mounting aperture.

According to a preferred practice, the gas sensor is a removable and replaceable sensor that is easily and conveniently mounted within the aperture 42, as well as removed therefrom. According to this embodiment, the gas-sensing mask 20 provides for a system that can continuously monitor the respiration of a patient during a selected time interval. The ability to remove and replace the gas sensor allows the attending clinician to continuously supply oxygen and to continuously monitor the patient's respiration by simply replacing the gas sensor 40 when necessary. The ability to replace the sensor provides for a reusable mask that reduces waste.

As used herein, the term "gas sensor" is intended to include any gas-sensing device that is capable of detecting the presence of a selected respired gas, such as carbon dioxide and oxygen, as is known in the art. The gas sensor preferably indicates directly or is coupled to appropriate structure that indicates the presence or absence of the respired gas. The gas sensor thus can include one or more appropriate indicators that are sensitive to changes in heat and pH, and most preferably includes an indicator which visually indicates the presence or absence of the gas, such as calorimetric indicators. As is known, a pH change occurs when carbon dioxide reacts with water to form carbonic acid ($H_2CO_3$). Hydrogen ions from the reaction then react with a color indicator, for example a redox indicator, to produce a color change which is visible to the human eye. Thus, when a colorimetric reaction takes place, the presence of carbon dioxide in the respired breath of the patient is easily and readily indicated. Similarly, the carbon dioxide in the respired gas may react with a heat sensitive indicator to yield the desired calorimetric change. Temperature sensitive indicators which change color in response to a predetermined temperature change, such as those produced and manufactured by Sharn, Inc., of Tampa, Fla., U.S.A., and which are sold under the trade designation Temp-A-Strip, can also be used to indicate the presence of carbon dioxide in the respired gas.

Preferred calorimetric indicators which produce a color change in the presence of carbon dioxide include chromogenic pH-sensitive indicators, which are known in the art and are fully described in U.S. Pat. No. 4,728,499 of Fehder, the teachings of which are hereby incorporated by reference. The chromogenic indicators, e.g., visual indicators, progressively change color in the presence of carbon dioxide through a range of visually distinct colors (e.g., shades of color) depending upon the concentration of carbon dioxide, thus allowing the gas sensor to yield a meaningful rapid response signal in the presence of the respired gas. Examples of suitable chromogenic pH sensitive indicators which can be used in the gas sensor 40 include metacresol purple, thymol blue, cresol red, phenol red, xylenol blue, a 3:1 mixture of cresol red and thymol blue, bromthymol blue, neutral red, phenolphtalein, rosolic acid, α-naphtholphtalein, orange I, bromcresol purple, bromphenol red, p-nitrophenol, m-nitrophenol, curcumin, quinoline blue, thymolphthalein and mixtures thereof.

Other chemical reagents are also contemplated by the present invention. These reagents include any compound that absorbs and reacts with the gaseous carbon dioxide thereby producing a pH change, which then reacts with the chromogenic indicator to produce a color change. Because of the slightly acidic nature of carbon dioxide, the carbon dioxide-absorbing chemical is usually alkaline in nature in order to ensure a rapid and total reaction with carbon dioxide, and to ensure a sufficient pH change to change the color of the visual indicator. The carbon dioxide absorbent compounds that can be used include the oxides and hydroxides of the alkaline metals and alkaline earth metals, such as barium oxide, barium hydroxide, calcium oxide, calcium hydroxide, sodium hydroxide, magnesium oxide, potassium hydroxide, lithium hydroxide and combinations thereof. Similarly, amphoteric oxides or hydroxides of the transition metals that can react with carbon dioxide, such as zinc oxide, can also be used either alone or in combination with the alkaline metal and alkaline earth oxides and hydroxides. Similarly, commercially available hydrozene compounds, such as those used in the drager tube atmosphere analyzing device, available from Drager Werk AG, Germany, can be used in accordance with the present invention. The visual indicators visually detect the interaction of the carbon dioxide with the carbon dioxide absorbing compound. Thus, the indicators change color in relation to a pH change that occurs in this environment. Normally, the visual indicator exhibits its alkaline color within the gas sensor 40 until the carbon dioxide contacts and reacts with the absorbent compound, causing a chemical reaction and pH drop. The visual indicator will then change color to its acidic color. These visual indicators include ethyl violet, thymolphthalein, alizarin yellow, phenolphthalein, thymol blue, ethyl bis(2,4-dimethylphenol)acetate, p-naphthol benzene, o-cresolphthalein and alizarin. Graduations may be disposed on the gas sensor to prove a quantitative indication of carbon dioxide.

The indicator of the gas sensor can also comprise a porous glass support having a pH sensitive dye, water and a phase transport enhancer adsorbed thereon. In addition, the indicator may further comprise a buffer. The support material may be any material upon which a dye can be adsorbed or covalently attached. Various porous and non-porous supports may be used as the support including controlled poor glasses, ion exchange resins, celluloses, collagens, polymerics such as polyacrilimides, polymethylacrylates, polystyrenes, polylycines, polyurethanes, polyesters, and polysiloxanes. Such supports are well known to those of ordinary skill in the art and may be prepared according to conventional methods. The properties of the surface area, ability to adsorb the dye, and lack of a strong hydrophobisity affects the performance of the indicator and thus, can be selected to improve the indicator function. The pH sensitive dyes suitable for use with the support material and which change color in response to changes in pH are commercially available and known to those of ordinary skill in the art. Examples of pH sensitive dyes include phenol red, bromothymol blue, bromocresol purple rosolic acid phenolphthalein, cresol red, thymol blue, m-Nitrophenol, xylenol blue, curcumin, m-Cresol purple, cresolphthalein, thymolphthalein, malachite green, N,N-Dimethylaniline, bromocresol green. The use of glass supports and pH sensitive dyes are fully disclosed in U.S. Pat. No. 5,005,572 of Raemer et al., the teachings of which are hereby incorporated by reference.

The gas sensor 40 of the present invention is preferably a carbon dioxide sensor having a colorimetric indicator that allows for a quick and easy visually determination of the respiration or the presence of carbon dioxide in the breath of the patient. The preferred gas sensor 40 is a carbon dioxide gas sensor of the type produced by Nellcor incorporated of Hayward, Calif., U.S.A. In a preferred embodiment of the present invention, the gas sensor 40 turns purple on inhalation and yellow on exhalation. The specific quantity of carbon dioxide present in the respired gas of the patient will induce the colorimetric indicator to change color in a range of selected colors, and typically between purple and yellow.

The preferred gas sensor 40 includes a transparent window formed on an outer surface 40A, FIG. 3, which allows a clinician to easily view the colorimetric change that occurs in the sensor during use. With reference to FIGS. 1 through 3, and with particular reference to FIG. 3, the sensor aperture 42 is located in the intermediate portion 20B of the mask 20 and overlies either the nose and/or mouth of the patient. This location positions the gas sensor 40 at a location relatively close to the nose and mouth of the patient and in relatively close fluid communication therewith. The illustrated baffles 44 are located about the sensor aperture 42. The baffles 44 preferably comprise a set of outwardly projecting members 44A–44D that have a substantially rigid body 44A and a leg portion 44B. The leg portions 44B are preferably secured to the inner surface 20E of the mask by a number of conventional techniques, including sonic welding. The baffles 44A–44D, FIG. 2, preferably channel the respired gas from the patient to the backside, leftmost portion in FIG. 3, of the sensor 40, to prevent substantial mixing of the respired gas with the inflowing oxygen.

The gas sensor 40 indicates the presence or absence of the respired gas by changing colors, as set forth above. Alternatively, the gas sensor can be coupled to appropriate circuitry that indicates the presence or absence of the respired gas. The present invention thus further contemplates the use of an electrical indicator, such as a gas-sensitive electrode or solid state device, e.g., transistor, which is adapted to detect changes in the ambient chemical environment of the gas sensor 40 or the fluid environment of the mask 20. The electrical indicator can be a component of the gas sensor 40 or can be coupled to the gas sensor or mask 20 of the present invention. The indicator as contemplated by the invention can include further electrical circuitry, such as the control unit 58 and attached peripheral devices.

With reference to FIG. 1, the gas-sensing mask 20 of the present invention is further coupled to associated electrical circuitry that is activatable upon the presence or absence of a respired gas. According to one mode of practice, a gas-sensitive electrode is secured to the ventilation aperture 28 and is coupled to electrical lead 46. The electrode is preferably a carbon dioxide sensitive electrode that produces a corresponding electrical signal in the presence of carbon dioxide. The electrical signal produced by the carbon dioxide sensitive electrode is received by the control unit 48, which in turn activates either display monitor 52 or alarm unit 56. The particular display device can be selected via switches or control knobs or by other electrical circuitry, e.g., a multiplexer, that is electrically associated with, or forms part of, the control unit 48, as is readily apparent to those of ordinary skill in the field of electrical engineering.

Carbon dioxide sensitive electrodes are known in the art, and typically use a silver/silver halide internal reference electrode and a quinhydrone electrode as a pH sensor to detect changes in pH induced by carbon dioxide, which penetrates an overcoated carbon dioxide-permeable membrane, as described in U.S. Pat. No. 3,730,868 of Niedrach. Further carbon dioxide sensitive electrodes include hydrogen ion electrodes that include a flexible, metallic, elongated electrode lead formed of silver wire and which is electronically conducting and has an electrochemically active region at one end. The electrochemically active region can be, for example, silver and a silver halide. An outer membrane encapsulates this electrochemically active region and preferably contains an electrolytic solution that contains an ion that enters equilibrium with the electrochemical region 19, such as a halide ion. Examples of other electrodes suitable for use with the gas-sensing mask 20 include conventional pH sensitive electrodes, such as glass electrodes, hydrogen electrodes, quinhydrone electrodes and antimony electrodes, with the glass type electrodes being the most preferred. Other suitable electrical components include pH sensitive field-effect transistors.

According to another practice of the invention, the calorimetric change generated within the sensor 40 is detected by a suitable electrical detector associated with the sensor 40. For example, the foregoing carbon dioxide electrode can be mounted on or in the gas sensor 40 and can produce a corresponding electrical signal in the presence of carbon dioxide. The electrical signal produced by the carbon dioxide sensitive electrode is transferred along lead 50 to the control unit 48, which in turn activates either display monitor 52 or alarm unit 56.

According to still another practice, and as is known, every color corresponds to one or more different wavelengths of light. Thus, a change in color from one wavelength to another may be detected by suitable electronic circuitry or an optical detection system that is coupled to the gas sensor 40. This color detection system preferably generates electrical signals characteristic of the colorimetric change within the gas sensor 40 and is transferred to the control unit 48 by electrical lead 50. The control unit 48 receives the electrical signals generated by the detection system and triggers either the monitor display 52 or the alarm 56.

As mentioned above, a significant aspect of the present invention is the ability of the mask 20 to continuously monitor the respiration of the patient. By employing a calorimetric carbon dioxide sensor, the gas-sensing mask visually indicates the presence or absence of a selected respired gas, such as carbon dioxide. Thus, hospital clinicians working or located in an area within visual range of the gas-sensing mask 20 can monitor the patient's breathing from afar, rather than requiring the clinician to be located relatively close or adjacent to the patient. Thus, by simply looking at the gas-sensing mask 10 the hospital personnel can rapidly and instantaneously detect changes in the respiratory rate or breathing faculty of the patient. In order to enhance the easy viewing of the respiratory rate of the patient, the sensor 40 can be appropriately sized to allow easy viewing from a number of distances and locations relative to the patient.

In operation, the gas-sensing mask 20 is placed over the patient's face and secured to the patient's head by the strap 16 and clip 26. If the gas sensor 40 is not already mounted within the mask, the sensor is disposed therein at this juncture. The oxygen adapter is then matingly engaged with the female luer lock connector (if not already molded thereon) to provide a fluid lumen between the fluid chamber 24 of the mask 20 and the oxygen source. The patient's respiration is then monitored.

According to the teachings of the present invention, the patient's breathing can be monitored in a number of ways. During monitoring, when the patient inhales, the preferred gas sensor 40 of the invention calorimetrically detects the presence of oxygen in the fluid chamber 24 by changing to a selected color, e.g., purple. When the patient exhales, the carbon dioxide present in the respired gas is channeled by baffles 44 to the sensor which then changes to a second selected color, e.g., yellow. This continually changing series of colors visually indicates the breathing rate and faculty of the patient.

According to another practice of the invention, the gas sensor selectively triggers a remote indicating device, which preferably includes the control unit 48. The control unit 48 in turn triggers either the alarm 56 or the monitor 52. Thus, the attending clinician is rapidly notified of a change in the respiratory pattern of the patient by either peripheral device. Alternatively, a pH electrode or transistor is coupled to the mask 20 or gas sensor and is connected to the control unit 48. A change in pH created electrically by the presence of carbon dioxide induces the device to emit electrical signals. These electrical signals are coupled to the control unit 48 by leads 46 or 50. The control unit then triggers either the monitor 52 or the alarm 56.

FIG. 4 illustrates a second embodiment of the gas-sensing mask 80 of the present invention. The illustrated mask 80 includes a non-porous housing 82 that has a top portion 82A, an intermediate portion 82B, and a bottom portion 82C. The bottom portion 82C has formed therein a fluid conduit aperture that has a female luer lock connector 84. A mating fluid adapter 86 couples to the female luer connector 84, as shown.

The illustrated intermediate portion 82B of the mask includes an upwardly extending mask portion 90 which terminates in a sensor mounting aperture 92. The upwardly extending mask portion can be a separate piece that is welded to the housing 82 or can be integrally molded with the housing to form a one-piece, e.g., unitary, structure.

A gas sensor 96 according to the present invention is mounted within the sensor mounting aperture 92 and intimately contacts the upwardly extending mask portion 90. The gas sensor 96 is preferably similar (in structure and operation) to the gas sensor 40 of FIGS. 1–3. A set of baffles 100 is preferably mounted on an interior portion of the mask or form part of the upwardly extending portion if provided as a separate piece, to channel respired gases to the gas sensor 96.

A ventilation aperture 102, identical to those described above in relation to FIGS. 1 through 3, is formed on opposite sides of the gas mask 80. The gas mask can be secured to the head of the patient by the illustrated straps and pressure tab, as described above.

The illustrated gas sensor 96 can be coupled to the control unit 48 of FIG. 1 by suitable electrical leads, as described above, and can further operate in conjunction with the above-described carbon dioxide sensitive electrodes or transistors, and with known optical detection systems.

This embodiment of the gas mask 80 illustrates the different mask housing designs which can be used in accordance with the teachings of the present invention, and which enable a gas sensor to be directly mounted thereon and to be coupled to an oxygen source.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A gas detecting mask, comprising
    a non-porous housing sized to seat over the nose and mouth of a subject, said mask having aperture means forming an aperture in a bottom portion of said housing, said aperture being sized to seat a fluid conduit, and
    a passive colorimetric gas sensor disposed within a corresponding sensor mounting aperture formed in said mask for sensing one or more selected gases respired by the subject, said colorimetric gas sensor visually indicating the presence or absence of the respired gas, wherein said sensor when mounted within said mounting aperture being integrally formed with said housing and disposed in intimate contact therewith, such that a portion of said sensor is mounted to the outer external surface of said mask, and said calorimetric change of color of said gas sensor in the presence or absence of the respired gas is viewable externally of said mask.

2. The mask of claim 1 wherein said housing includes a substantially dome-shaped intermediate portion forming a fluid chamber configured to seat over the mouth and nose of the subject, said mask further including ventilation means forming a ventilation aperture in opposite sides of said mask for ventilating gases within said chamber.

3. The mask of claim 1 wherein said gas sensor is removably and replaceably mounted within said sensor mounting aperture.

4. The mask of claim 1 wherein said calorimetric gas sensor generates a first color in the absence of the respired gas and generates a second, different color in the presence of the gas.

5. The mask of claim 1 wherein said calorimetric gas sensor is a carbon-dioxide sensor that senses end-tidal carbon dioxide respired by the subject, said gas sensor including visual indicator means for generating a first color in the absence of carbon dioxide and a second, different color in the presence of carbon dioxide.

6. The mask of claim 1 further including baffle means forming a baffle coupled to and integrally formed with a central portion of the mask for channeling the gas to said sensor mounting aperture, and thus to said colorimetric gas sensor, without impeding the flow of oxygen introduced to the mask through said aperture in the bottom of the mask from intermingling with the respired gas which is introduced to the sensor.

7. The mask of claim 1 wherein said housing comprises an oxygen-delivery mask.

8. A face mask comprising a non-porous housing having a top and bottom portion and a dome-shaped intermediate portion having an outer surface disposed therebetween, said mask being sized to seat over the nose and mouth of a subject and forming a fluid chamber when seated thereover, said housing including
first aperture means forming a first aperture within said dome-shaped intermediate portion of said housing, said first aperture extending from an inner surface of said mask to an outer surface of said mask,
second aperture means forming a second aperture within said bottom portion of said housing for mounting a fluid conduit, and
a passive colorimetric gas sensor for sensing the presence or absence of a respired gas mounted within said first aperture such that a portion of said sensor which visually indicates the presence or absence of the respired gas extends beyond the outer surface of said housing when mounted therein, such that the exposed portion of said sensor is viewable externally of said mask.

9. The mask of claim 8 further comprising ventilation means formed in at least one side of said mask for ventilating gas within said fluid chamber.

10. The mask of claim 8 wherein said housing includes means for channeling a respired gas from the subject to the first aperture.

11. A gas-sensing, oxygen delivering system for delivering a gas to and sensing a gas produced by a subject, said system comprising
a non-porous mask having first aperture means forming a first aperture in a bottom of said mask and second aperture means forming a second aperture in an intermediate portion of said mask, said aperture extending between an outer surface of said mask and an inner surface of said mask, said mask being sized to seat over the nose and mouth of the subject and forming a gas chamber when seated thereover,
a passive colorimetric gas sensor mountable within said second aperture and in fluid communication with said chamber for sensing the respired gas, said colorimetric gas sensor visually indicating the presence or absence of the gas, wherein a portion of said sensor when mounted within said second aperture is disposed in intimate contact with the outer external surface of said mask, and said colorimetric change of color of said gas sensor in the presence or absence of the respired gas is viewable externally of said mask, and
gas delivery means for delivering a selected gas to said chamber, said gas delivery means including conduit means having a first end coupled to said first aperture and a second end coupled to a gas supply for delivering said gas through said conduit means to said chamber.

12. The system of claim 11 wherein said colorimetric gas sensor is a carbon dioxide sensor.

13. The system of claim 11 further comprising ventilation means for ventilating gases from said chamber to an external environment.

14. A method for monitoring the respiration of a subject, comprising the steps of
placing a non-porous mask over the mouth and nose of the subject forming a fluid chamber when mounted thereover, said mask having a first aperture formed therein that extends between an outer surface and an inner surface,
passively and calorimetrically sensing a selected respired gas from the subject by a calorimetric gas sensor mounted within said first aperture, said sensor being integral with and disposed in contact with said mask such that a portion of said gas sensor extends beyond the mask and is viewable externally of said mask, said sensor visually indicating the presence or absence of said respired gas, and
monitoring said respiration of the subject by said visual indication of said sensed respired gas.

15. The method of claim 14 further comprising the step of delivering oxygen to said chamber.

16. The method of claim 15 further comprising the step of ventilating gas from said chamber to an external environment.

17. A method for visually indicating the respiration of a subject, comprising the steps of
placing a non-porous mask over the mouth and nose of the subject forming a fluid chamber when mounted thereover, said mask having a sensor mounting aperture extending between an outer surface of the mask and an inner surface of the mask and a fluid aperture formed therein,
passively and colorimetrically sensing a selected respired gas from the subject by a colorimetric gas sensor mounted within said sensor mounting aperture, said sensor being integral with and disposed in contact with said mask such that a portion of said sensor is exposed to an external environment and is viewable externally of the mask,
introducing oxygen to the fluid chamber through the fluid aperture, and
visually indicating the presence or absence of said respired gas.

18. A gas-sensing, oxygen delivering face mask having a fluid aperture for the introduction of oxygen, the face mask being sized to seat over a patient's nose and mouth and adapted to deliver oxygen thereto, the face mask being formed of a non-porous material and having an inner surface and an outer surface exposed to an external environment and viewable by a person other than the patient, the mask comprising means forming an aperture in a central portion of the mask, said aperture extending between the inner surface and the outer surface thereof, and a passive colorimetric gas-sensor mounted within the aperture and having visual indicator means for visually indicating the presence or absence of a respired gas, wherein a portion of said gas sensor having said visual indicator means is exposed to an external environment and viewable therefrom, and wherein a portion of said gas sensor opposite said portion exposed to the external environment is disposed in fluid communication with the respired gas to allow the gas sensor to visually indicate the presence or absence of the gas, whereby the portion of the gas sensor exposed to the external environment and which visually indicates the presence or absence of the respired gas allows a person other than the patient to view the breathing cycle of the patient from a variety of distances.

* * * * *